(12) United States Patent
Lai et al.

(10) Patent No.: US 10,604,634 B1
(45) Date of Patent: Mar. 31, 2020

(54) METHOD FOR MANUFACTURING TEREPHTHALIC ACID AND SYSTEM THEREOF

(71) Applicant: Far Eastern New Century Corporation, Taipei (TW)

(72) Inventors: Po-Chen Lai, Taoyuan (TW); Jyun-Sian Lee, Taoyuan (TW); Sih-Hao Chiang, Taoyuan (TW); Chin-Shui Liang, Taoyuan (TW); Hsiang-Chin Tsai, Taoyuan (TW)

(73) Assignee: Far Eastern New Century Corporation, Taipei (TW)

( * ) Notice: Subject to any disclaimer, the term of this patent is extended or adjusted under 35 U.S.C. 154(b) by 0 days.

(21) Appl. No.: 16/254,623

(22) Filed: Jan. 23, 2019

(30) Foreign Application Priority Data

Sep. 26, 2018 (TW) .............................. 107133898 A

(51) Int. Cl.
| | |
|---|---|
| *C08J 11/26* | (2006.01) |
| *C07C 51/09* | (2006.01) |
| *C07C 51/43* | (2006.01) |
| *B29B 17/04* | (2006.01) |
| *C08J 11/16* | (2006.01) |

(52) U.S. Cl.
CPC ............... *C08J 11/26* (2013.01); *B29B 17/04* (2013.01); *C07C 51/09* (2013.01); *C07C 51/43* (2013.01); *C08J 11/16* (2013.01); *B29B 2017/0468* (2013.01); *C08J 2367/02* (2013.01)

(58) Field of Classification Search
None
See application file for complete search history.

(56) References Cited

U.S. PATENT DOCUMENTS 6,031,128 A * 2/2000 Roh ..................... C07C 51/09
422/184.1
6,580,005 B1   6/2003 Yazaki et al.

FOREIGN PATENT DOCUMENTS

| CN | 102532815 A | 7/2012 | |
|---|---|---|---|
| CN | 102532591 B | 12/2013 | |
| GB | 2123403 A * | 2/1984 | ............. C07C 29/09 |

* cited by examiner

*Primary Examiner* — Clinton A Brooks
*Assistant Examiner* — Kofi Adzamli
(74) *Attorney, Agent, or Firm* — CKC & Partners Co., LLC

(57) ABSTRACT

A method for manufacturing terephthalic acid includes the following operations: providing a raw material, in which the raw material includes a first raw material including polyethylene terephthalate; performing a depolymerization reaction on the first raw material to form a depolymerization product, in which the depolymerization product includes disodium terephthalate; performing a decolorization process on the disodium terephthalate to form decolorized disodium terephthalate and precipitated sludge; separating the decolorized disodium terephthalate and the sludge; and forming terephthalic acid from the decolorized disodium terephthalate after separating the decolorized disodium terephthalate and the sludge.

7 Claims, 2 Drawing Sheets

100

110 — A raw material is provided. The raw material includes a first raw material comprising polyethylene terephthalate.

120 — A depolymerization reaction is performed on the first raw material to form a depolymerization product. The depolymerization product includes disodium terephthalate.

130 — A decolorization process is performed on the disodium terephthalate to form decolorized disodium terephthalate and precipitated sludge.

140 — The decolorized disodium terephthalate and the sludge are separated.

150 — Terephthalic acid is formed from the disodium terephthalate.

METHOD FOR MANUFACTURING TEREPHTHALIC ACID AND SYSTEM THEREOF

RELATED APPLICATIONS

This application claims priority to Taiwan Application Serial Number 107133898, filed Sep. 26, 2018, which is herein incorporated by reference.

BACKGROUND

Field of Invention

The present invention relates to a method for manufacturing terephthalic acid and a system thereof.

Description of Related Art

Polyesters have excellent mechanical strength and chemical stability, so they have been widely used in various applications. However, due to the different compositions, and also different additives, of different products, the difficulty of recycling polyesters in different products is increased.

The current polyester recycling methods are only suitable for polyesters with relatively simple components, such as those used only for bottle flakes of polyethylene terephthalate or scrap materials or edge-trim materials of polyethylene terephthalate in factories.

For the foregoing reasons, there is a need to provide a method and a system suitable for various polyester wastes.

SUMMARY

A method for manufacturing terephthalic acid is provided. The method for manufacturing terephthalic acid comprises the following operations: providing a raw material, in which the raw material includes a first material comprising polyethylene terephthalate; performing a depolymerization reaction on the first raw material to form a depolymerization product, in which the depolymerization product comprises disodium terephthalate; performing a decolorization process on the disodium terephthalate to form decolorized disodium terephthalate and precipitated sludge; separating the decolorized disodium terephthalate and the sludge; and forming terephthalic acid from the decolorized disodium terephthalate after separating the decolorized disodium terephthalate and the sludge.

In the foregoing, the raw material further comprises a second raw material. The second raw material consists essentially of a polymer other than polyethylene terephthalate, and the operation of providing the raw material comprises separating the first raw material and the second raw material.

In the foregoing, the operation of providing the raw material further comprises: breaking the first raw material by using a crushing device after separating the first raw material and the second raw material.

In the foregoing, the depolymerization product further comprises a solid waste.

In the foregoing, the method for manufacturing terephthalic acid further comprises making the second raw material, the solid waste, and the sludge into a refuse derived fuel.

In the foregoing, the method for manufacturing terephthalic acid further comprises separating the disodium terephthalate and the solid waste.

In the foregoing, the operation of performing the decolorization process on the disodium terephthalate comprises adding a flocculating agent and activated carbon to the disodium terephthalate.

In the foregoing, the operation of forming the terephthalic acid from the decolorized disodium terephthalate comprises: adding sulfuric acid to the decolorized disodium terephthalate to obtain the terephthalic acid.

In the foregoing, the method for manufacturing terephthalic acid further comprises rinsing the terephthalic acid with water and drying the rinsed terephthalic acid to purify the terephthalic acid.

The invention provides a system for manufacturing terephthalic acid. The system for manufacturing terephthalic acid comprises a depolymerization reactor, a decolorization reactor, a second separation unit, and a crystallization reactor. The depolymerization reactor is configured to perform a depolymerization reaction on a first raw material comprising polyethylene terephthalate in a raw material to form a depolymerization product, in which the depolymerization product comprises disodium terephthalate. The decolorization reactor is configured to perform a decolorization process on the disodium terephthalate so as to form decolorized disodium terephthalate and precipitated sludge. The second separation unit is configured to separate the decolorized disodium terephthalate and the sludge. The crystallization reactor is configured to form terephthalic acid from the decolorized disodium terephthalate after the second separation unit separates the decolorized disodium terephthalate and the sludge.

In the foregoing, the system for manufacturing terephthalic acid further comprises a sorting and screening device, a crushing device, and a purification reactor. The sorting and screening device is configured to perform a separation process on the raw material. The raw material further comprises a second raw material, in which the second raw material consists essentially of a polymer other than polyethylene terephthalate. The separation process comprises separating the first raw material and the second raw material. The crushing device is configured to break the first raw material separated by the sorting and screening device. The purification reactor is configured to rinse the terephthalic acid with water and dry the rinsed terephthalic acid to purify the terephthalic acid.

In the foregoing, the depolymerization product further comprises a solid waste.

In the foregoing, the system for manufacturing terephthalic acid further comprises a refuse derived fuel producing device. The refuse derived fuel producing device is configured to make the second raw material, the solid waste, and the sludge into a refuse derived fuel.

In the foregoing, the system for manufacturing terephthalic acid further comprises a first separation unit. The first separation unit is configured to separate the disodium terephthalate and the solid waste.

It is to be understood that both the foregoing general description and the following detailed description are by examples, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings, FIG. 1 depicts a flowchart of a method for manufacturing terephthalic acid according to some embodiments of this invention.

DESCRIPTION OF THE EMBODIMENTS

Figure 2:
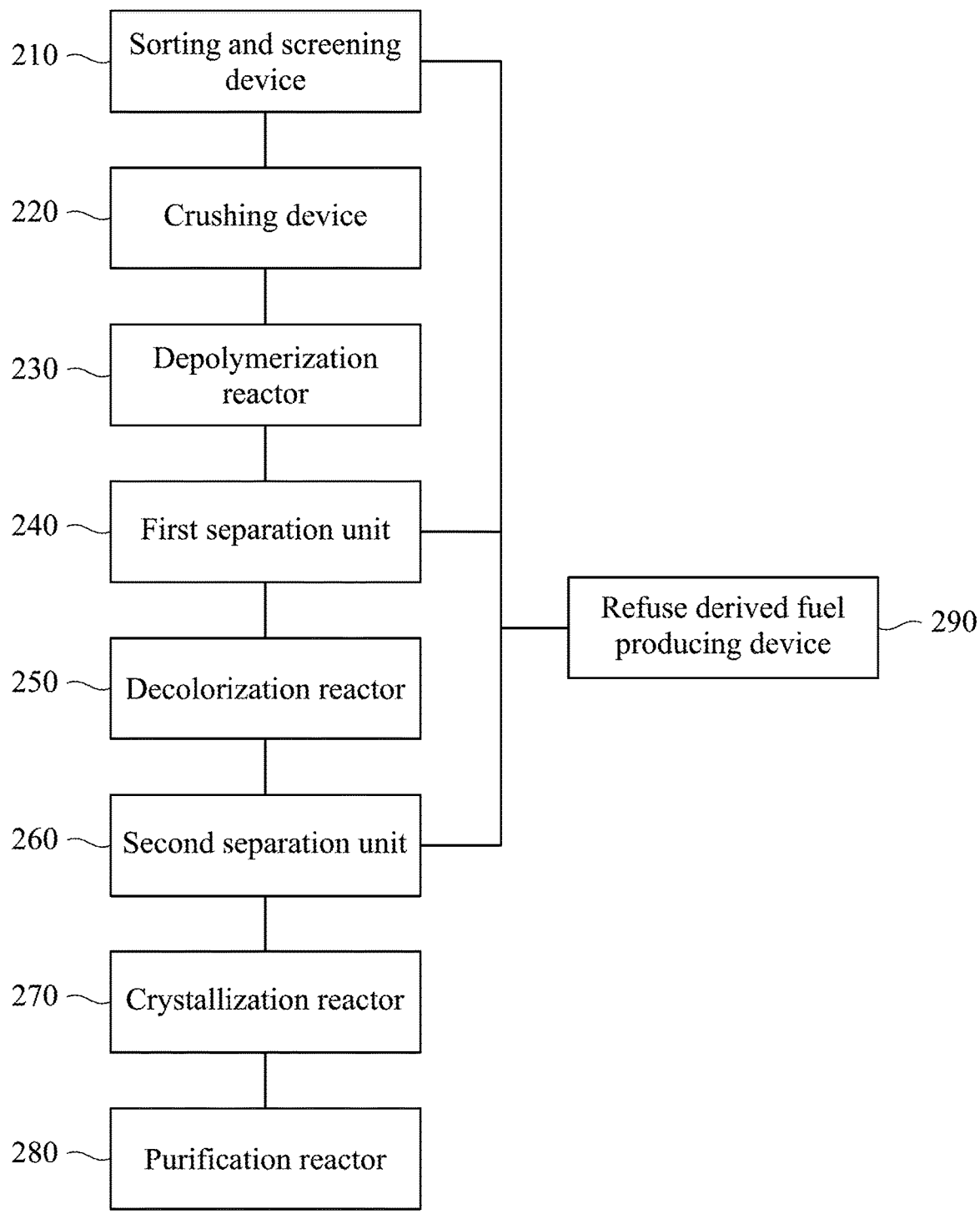
FIG. 2 depicts a system for manufacturing terephthalic acid according to some embodiments of this invention.

The following disclosure provides many different embodiments, or examples, for implementing different features of the provided subject matter. Specific examples of components and arrangements are described below to simplify the present disclosure. These are, of course, merely examples and are not intended to be limiting. For example, the dimensions of the elements are not limited by the scope or value of the disclosure, but may depend on the process conditions and/or desired characteristics of the elements.

Unless the context clearly dictates otherwise, the singular terms used herein include plural referents. In at least one of the embodiments of the present disclosure, by way of a specific reference to the "one embodiment", a particular feature, structure, or characteristic is indicated. When a particular reference is made, it is not necessary to refer to the same embodiment, and further, in one or more embodiments, these particular features, structures, or characteristics may be combined with each other as appropriate.

The present invention provides a method for manufacturing terephthalic acid. The raw material of which may be any waste containing polyester. In greater detail, the raw material of the method for manufacturing terephthalic acid according to the present invention may be a textile, a bottle flake or other waste containing polyester.

FIG. 1 depicts a flowchart of a method 100 for manufacturing terephthalic acid according to some embodiments of the present invention. The method 100 comprises an operation 110, an operation 120, an operation 130, an operation 140, and an operation 150. In operation 110 of FIG. 1, a raw material is provided. The raw material includes a first raw material. The first raw material includes polyethylene terephthalate. In some embodiments, the raw material further includes a second raw material. The second raw material consists essentially of a polymer other than polyethylene terephthalate. The first raw material may be, for example, a waste, such as a textile or a bottle flake comprising polyethylene terephthalate. The second raw material may be, for example, cotton, nylon, or other waste, such as a textile or a bottle flake composed of a polymer other than polyethylene terephthalate.

In an embodiment which the raw material includes the first raw and the second raw material, the operation 110 includes separating the first raw material and the second raw material. The near-infrared light may be used to analyze the composition of the raw material, and then the first raw material and the second raw material are separated. In an embodiment which the raw material is the textile or the bottle flake, the first raw material may be broken by a crushing device after separating the first raw material and the second raw material. Breaking the first raw material can greatly increase the surface area of the subsequent chemical reaction, thus improving the efficiency of subsequent manufacturing of terephthalic acid.

In operation 120, a depolymerization reaction is performed on the first raw material to form a depolymerization product. In some embodiments, the depolymerization product comprises disodium terephthalate. In the depolymerization reaction of operation 120, ethylene glycol, sodium carbonate, and zinc acetate may be added to carry out the reaction. In some embodiments, an amount of ethylene glycol is 2 to 15 times (such as 5 times, 8 times, or 12 times) a weight of the first raw material. An amount of sodium carbonate is 1 to 2 times a mole number of the polyethylene terephthalate in the first raw material. An amount of zinc acetate is 1000 to 10000 ppm by weight of the polyethylene terephthalate. In the depolymerization reaction of some embodiments, the reaction is carried out at a range from 160° C. to 200° C. for 4 to 12 hours. The disodium terephthalate formed by the depolymerization reaction is a yellowish solid. In some embodiments, the depolymerization product further includes a solid waste. Separation of the disodium terephthalate and the solid waste may be achieved by adding pure water to dissolve and filter the disodium terephthalate.

After that, in operation 130, a decolorization process is performed on the disodium terephthalate produced by the depolymerization reaction to form decolorized disodium terephthalate and precipitated sludge. In some embodiments, the decolorization process is performed by using the disodium terephthalate separated from the solid waste. Since the separated disodium terephthalate is an aqueous solution, a flocculating agent and a coagulant aid may be directly added to the aqueous solution of disodium terephthalate to flocculate and precipitate impurities. Additionally, in some embodiments, activated carbon may be added to the aqueous solution of disodium terephthalate to remove the yellowish color so as to form the above decolorized disodium terephthalate. In some embodiments, the above precipitated sludge comprises a flocculated precipitate and the activated carbon. In some embodiments, the flocculating agent comprises but not limited to alum, aluminum sulfate, aluminum chloride, or combinations thereof. In some embodiments, the above coagulant aid comprises but not limited to quicklime, chlorine, or a combination thereof.

In operation 140, the decolorized disodium terephthalate and the sludge are separated. After the flocculated precipitate and the activated carbon are removed by filtration, the decolorized disodium terephthalate separated from the sludge can be obtained. The decolorized disodium terephthalate is in a state of an aqueous solution.

Then, in operation 150, terephthalic acid is formed from the disodium terephthalate. In some embodiments, sulfuric acid is dripped into the decolorized aqueous solution of disodium terephthalate to form the terephthalic acid. In greater detail, the disodium terephthalate in the solution is converted into a plurality of terephthalic acid particles. In some embodiments, a concentration of the sulfuric acid dripped into the decolorized aqueous solution of disodium terephthalate is from 5 to 65 percentage by weight (wt %). In some embodiments, during the process that the sulfuric acid is dripped into the decolorized aqueous solution of disodium terephthalate, a temperature of the solution is controlled between 25° C. and 85° C.

It is noted that the terephthalic acid formed from disodium terephthalate comprises a little impurity. Hence, the terephthalic acid needs to be purified according to certain embodiments. In some embodiments, the purification process removes the sodium salt in the terephthalic acid by water washing, and the washed terephthalic acid is dried. In some embodiments, the washed and dried terephthalic acid has a b* value of 0.4 to 2.0 and an acid value of 650 to 677 KOHmg/g. The CIELAB color system (L*, a*, b*) is usually used to describe the color visible to the naked eye. The above b* value represents a b* value of a position between the yellow and blue colors in the CIELAB color system (L*, a*, b*). In greater detail, a negative b* value indicates blue and a positive b* value indicates yellow. The acid value of the terephthalic acid manufactured according to the present invention is between 650 and 677 KOHmg/g, thus showing a higher purity. In greater detail, if terephthalic acid having an excessively low acid value (for example, less than 650 KOHmg/g) is used, incomplete polymerization is caused in subsequent applications. Since the terephthalic acid manufactured according to the present invention has a higher level of impurity, this situation can be avoided.

After operation 150, the method 100 for manufacturing terephthalic acid may perform some other operations. In certain embodiments, the second raw material separated in operation 110, the solid waste separated in operation 120, and the sludge separated in operation 140 are made into a refuse derived fuel. In some embodiments, the refuse derived fuel is a fifth type of refuse derived fuel (RDF-5). As mentioned previously, the second raw material consists essentially of the polymer other than polyethylene terephthalate, and the solid waste and sludge are by-products of the above method for manufacturing terephthalic acid. The present invention reuses the raw material and by-products that can not be used in the method for manufacturing terephthalic acid, and a calorific value of the fifth type of refuse derived fuel, which can be produced by compression and then reformation, can reach 3500-5000 kcal/kg. Fuels having a calorific value below 3500 kcal/kg according to the prior art have poor combustion efficiencies, and are not suitable for use as fuels. Therefore, the process waste of the present invention can be effectively reused for the preparation of RDF-5.

FIG. 2 depicts a system 200 for manufacturing terephthalic acid according to one embodiment of this invention. The system 200 for manufacturing terephthalic acid comprises a depolymerization reactor 230, a decolorization reactor 250, a second separation unit 260, and a crystallization reactor 270. The system 200 for manufacturing terephthalic acid 200 may further selectively comprise a sorting and screening device 210, a crushing device 220, a first separation unit 240, a purification reactor 280, and a refuse derived fuel producing device 290.

A raw material enters into the system 200 through the sorting and screening device 210, and the sorting and screening device 210 is configured to perform a separation process on the raw material. In some embodiments, the sorting and screening device 210 analyzes the textile composition by using the near-infrared light, and then separates different components in the raw material based on the analysis results. In some embodiments, the raw material includes a first raw material and a second raw material. The first raw material includes polyethylene terephthalate. The second raw material consists essentially of a polymer other than polyethylene terephthalate. In some embodiments, the above separation process is used to separate the first raw material from the second raw material.

The crushing device 220 is configured to perform a breaking process on the first raw material. Since the first raw material may be a textile, a bottle flake, or other waste containing polyester, the first raw material passing through the sorting and screening device 210 is transferred to the crushing device 220 to perform the breaking process. As a result, the first raw material having a smaller flake size is obtained.

The depolymerization reactor 230 is configured to perform a depolymerization reaction on the first raw material, which includes polyethylene terephthalate, in the raw material to form a depolymerization product. In some embodiments, the first raw material passing through the crushing device is transferred to the depolymerization reactor 230 to perform the depolymerization reaction. Disodium terephthalate and a solid waste are thus obtained. In some embodiments, ethylene glycol, sodium carbonate, and zinc acetate are added to the depolymerization reactor 230 to perform the depolymerization reaction.

After the depolymerization product is formed, the first separation unit 240 is configured to separate the disodium terephthalate and the solid waste. In greater detail, the first separation unit 240 separates the disodium terephthalate and the solid waste by adding pure water to dissolve and filter the disodium terephthalate. Hence, the separated disodium terephthalate is in a state of an aqueous solution.

The decolorization reactor 250 is configured to perform a decolorization process on the disodium terephthalate so as to form decolorized disodium terephthalate and precipitated sludge. In the decolorization reactor 250, a flocculating agent and activated carbon are added to the aqueous solution of disodium terephthalate to decolorize the disodium terephthalate. A flocculated precipitate generated by the flocculating agent and the activated carbon constitute the above sludge.

The second separation unit 260 is configured to separate the decolorized disodium terephthalate and the sludge. Since the decolorized disodium terephthalate is also in a state of an aqueous solution, the second separation unit 260 separates the decolorized disodium terephthalate and the precipitated sludge by filtration.

The crystallization reactor 270 is configured to form terephthalic acid from the disodium terephthalate after the second separation unit 260 separates the decolorized disodium terephthalate and the sludge. The terephthalic acid formed is solid. In greater detail, the crystallization reactor 270 converts the decolorized disodium terephthalate into a plurality of terephthalic acid particles. In some embodiments, sulfuric acid is added to the crystallization reactor 270 so as to perform a crystallization reaction.

The purification reactor 280 is configured to rinse the terephthalic acid generated by the crystallization reactor 270 with water and dry the rinsed terephthalic acid so as to purify the terephthalic acid. The purified terephthalic acid has a b* value of 0.4 to 2.0 and an acid value of 650 to 677 KOHmg/g.

The refuse derived fuel producing device 290 is configured to make the second raw material, the solid waste, and the sludge into a refuse derived fuel. The second raw material is separated by the sorting and screening device 210. The solid waste and the sludge are by-products respectively generated by the depolymerization reactor 230 and the decolorization reactor 250. This refuse derived fuel is a fifth type of refuse derived fuel and has a calorific value of 3500 to 5000 kcal/kg.

Some embodiments and comparative examples of the present invention are exemplarily described below.

Embodiment 1

Take 1 kg of textile. The textile contains 30% pure polyethylene terephthalate fabric, 35% polyethylene terephthalate blended fabric (where the polyethylene terephthalate content is 70%), and 35% non-polyethylene terephthalate fabric (such as cotton, nylon, and other blended fabric without polyethylene terephthalate, etc.). A sorting and screening device is used to separate the 650 g fabric containing polyethylene terephthalate and the remaining 350 g fabric. The 650 g fabric containing polyethylene terephthalate is broken down to have a side dimension of about 0.5 cm by using a crushing device.

The broken 650 g fabric containing polyethylene terephthalate is depolymerized with ethylene glycol, sodium carbonate, and sodium acetate at 160° C. for about 12 hours to form a solid of disodium terephthalate. Amounts of ethylene glycol, sodium carbonate, and zinc acetate are respectively ten times a weight of the fabric containing polyethylene terephthalate, 1.5 times a mole number of the polyethylene terephthalate, and 8000 ppm by weight of the polyethylene terephthalate. Then, the disodium terephthalate and ethylene glycol solution are separated by hot filtration at 140° C. After that, the disodium terephthalate is dissolved in five times its weight of pure water, and the insoluble matter is filtered again.

Thereafter, alum and a coagulant aid are added to an aqueous solution of disodium terephthalate. Amounts of the alum and the coagulant aid are both 1% by weight of the aqueous solution of disodium terephthalate. After stirring, a precipitate is formed. Then, activated carbon is added to the aqueous solution of disodium terephthalate. The activated carbon is used for absorbing residual impurities. An amount of the activated carbon is 10% by weight of the aqueous solution of disodium terephthalate. The above precipitate and activated carbon are removed by filtration to obtain a clarified aqueous solution of disodium terephthalate. The clarified aqueous solution of disodium terephthalate is measured by the Merck method 2518, and an American Dye Manufacturer's Institute (ADMI) value is less than 20. In the Merck method 2518, preparation of a sample is carried out by sequentially rinsing the filter paper with pure water and the sample, and then filtering 50 ml of the sample with the rinsed filter paper.

A 50 wt % sulfuric acid solution is dripped into the clarified aqueous solution of disodium terephthalate at 25° C. at a rate of 1 ml per minute to precipitate terephthalic acid. After that, the precipitated terephthalic acid is separated by filtration, and the terephthalic acid is rinsed five times by using 10 times its weight of pure water and dried to obtained purified terephthalic acid.

The remaining 350 g fabric, the insoluble matter in the depolymerization process, and the precipitate and the activated carbon are made into a fifth type of refuse derived fuel (RDF-5) by using a refuse derived fuel producing device.

Comparative Example 1

The same 1 kg of textile as embodiment 1 is taken to make a fifth type of refuse derived fuel by using the refuse derived fuel producing device.

Comparative Example 2

The same 1 kg of textile as embodiment 1 is taken and broken down to have a side dimension of about 0.5 cm by using the crushing device.

The broken fabric is depolymerized with ethylene glycol, sodium carbonate, and sodium acetate at 160° C. for about 12 hours to form a solid of disodium terephthalate. Amounts of ethylene glycol, sodium carbonate, and sodium acetate are respectively ten times the weight of the fabric containing polyethylene terephthalate, 1.5 times the mole number of the polyethylene terephthalate, and 8000 ppm by weight of the polyethylene terephthalate. Then, the disodium terephthalate and ethylene glycol solution are separated by hot filtration at 140° C. After that, the disodium terephthalate is dissolved in five times its weight of pure water, and the insoluble matter is filtered again to form an aqueous solution of disodium terephthalate.

A 50 wt % sulfuric acid solution is dripped into the aqueous solution of disodium terephthalate at 25° C. at a rate of 1 ml per minute to precipitate terephthalic acid. After that, the precipitated terephthalic acid is separated by filtration, and the terephthalic acid is rinsed five times by using 10 times its weight of pure water and dried to obtained purified terephthalic acid.

Table 1 is the various test data of each of the above embodiment and comparative examples. The calorific value is detected according to the waste calorific value detecting method, the b* value is measured by a colorimeter, and the acid value is measured by titration of potassium hydroxide.

TABLE 1

|  | Embodiment 1 | Comparative Example 1 | Comparative Example 2 |
| --- | --- | --- | --- |
| Fifth Type Of Refuse Derived Fuel (RDF-5) | | | |
| Yield (g) | 450 | 950 | Not Produced |
| Calorific Value (kcal/kg) | 3800 | 1000 | — |
| Purified Terephthalic Acid | | | |
| Yield (g) | 450 | Not Produced | 400 |
| b* Value | 0.7 | — | 20 |
| Acid Value (KOHmg/g) | 665 | — | 600 |

As can be seen from Table 1, Embodiment 1 produces 450 g of the fifth type of refuse derived fuel having a calorific value of 3800 kcal/kg and 450 g of purified terephthalic acid having a b* value of 0.7 and an acid value of 665 KOHmg/g. When compared with the weight of the raw material used (1 kg), application of the technical solution of the present invention can maximize the product with value in use and reduce the waste in the recycling process as possible.

Comparative Example 1 makes all the raw material into the fifth type of refuse derived fuel by using the refuse derived fuel producing device. Comparative Example 2 processes all the raw material by using the method for manufacturing terephthalic acid, such as depolymerization, precipitation, and purification, etc.

Comparative Example 1 produces 950 g of the fifth type of refuse derived fuel having a calorific value of 1000 kcal/kg. Although when compared with Embodiment 1, Comparative Example 1 produces a larger amount of fifth type of refuse derived fuel. However, the fifth type of refuse derived fuel of Comparative Example 1 has an excessively low calorific value and can not be used as a common fuel.

Comparative Example 2 produces 400 g of purified terephthalic acid having a b* value of 20 and an acid value of 600 KOHmg/g. When compared with Embodiment 1, less purified terephthalic acid is produced. In addition, the b* value of the purified terephthalic acid of Comparative Example 2 is much greater than that of Embodiment 1, thus showing that the product of Comparative Example 2 is yellowish in color. The purified terephthalic acid that is not decolorized will have a great impact on subsequent uses, thus increasing difficulty in processing and also leading to a reduction of application fields. In addition to that, the acid value of the purified terephthalic acid of Comparative Example 2 is lower than that of the Embodiment 1, so that the purified terephthalic acid of Comparative Example 2 may be incompletely reacted in subsequent applications.

It is noted that the raw material in Comparative Example 2 is not sorted and screened. Hence, the solid waste generated after depolymerization comprises cotton and other fabrics having a higher water absorption capacity to absorb an excessively high amount of ethylene glycol. As a result, the solid waste can not be made into a fifth type of refuse derived fuel by using the refuse derived fuel producing device. Therefore, Comparative Example 2 can not produce the fifth type of refuse derived fuel. Additionally, since the raw material of Comparative Example 2 comprises cotton and other fabrics having a higher water absorption capacity, more filtrate remains between the insoluble matter during filtration in the depolymerization operation, which causes less filtrate to be collected. The lesser filtrate amount collected affects the final yield of the terephthalic acid.

The method for manufacturing terephthalic acid and the system thereof according to the present invention can be used for recycling polyester. It is noted that the technical scheme of the present invention is applicable not only to the recycling of scrap materials or edge-trim materials of polyethylene terephthalate in factories, but also to the recycling of general waste textiles, bottle flakes or other wastes containing polyester.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method for manufacturing terephthalic acid comprising:
    providing a raw material, the raw material including a first material comprising polyethylene terephthalate and a second raw material consisting essentially of a polymer other than polyethylene terephthalate;
    performing a depolymerization reaction on the first raw material to form a depolymerization product, wherein the depolymerization product comprises disodium terephthalate and a solid waste;
    performing a decolorization process on the disodium terephthalate to form decolorized disodium terephthalate and precipitated sludge;
    separating the decolorized disodium terephthalate and the sludge; and
    forming terephthalic acid from the decolorized disodium terephthalate after separating the decolorized disodium terephthalate and the sludge; and
    making the second raw material, the solid waste, and the sludge into a refuse derived fuel.

2. The method for manufacturing terephthalic acid of claim 1, wherein the operation of providing the raw material comprises separating the first raw material and the second raw material.

3. The method for manufacturing terephthalic acid of claim 2, wherein the operation of providing the raw material further comprises:
    breaking the first raw material by using a crushing device after separating the first raw material and the second raw material.

4. The method for manufacturing terephthalic acid of claim 1, wherein the operation of performing the depolymerization reaction on the first raw material to form the depolymerization product comprises separating the disodium terephthalate and the solid waste.

5. The method for manufacturing terephthalic acid of claim 1, wherein the operation of performing the decolorization process on the disodium terephthalate comprises adding a flocculating agent and activated carbon to the disodium terephthalate.

6. The method for manufacturing terephthalic acid of claim 1, wherein the operation of forming the terephthalic acid from the decolorized disodium terephthalate comprises:
    adding sulfuric acid to the decolorized disodium terephthalate to obtain the terephthalic acid.

7. The method for manufacturing terephthalic acid of claim 1, further comprising rinsing the terephthalic acid with water and drying the rinsed terephthalic acid to purify the terephthalic acid.

* * * * *